United States Patent [19]
Roberts

[11] Patent Number: 4,537,994
[45] Date of Patent: Aug. 27, 1985

[54] SULFIDE METATHESIS
[75] Inventor: John S. Roberts, Bartlesville, Okla.
[73] Assignee: Phillips Petroleum Company, Bartlesville, Okla.
[21] Appl. No.: 542,960
[22] Filed: Oct. 18, 1983
[51] Int. Cl.³ .................. C07C 149/10; C07C 148/00
[52] U.S. Cl. ......................................... 568/59; 568/38
[58] Field of Search .................................. 568/59, 38
[56] References Cited
U.S. PATENT DOCUMENTS
3,076,848  2/1963  Laufer ................................. 260/609
4,059,636  11/1977 Kubicek .............................. 260/609
4,124,646  11/1978 Kawamura .......................... 260/609

FOREIGN PATENT DOCUMENTS
552641  2/1958  Canada .

Primary Examiner—Donald G. Daus
Assistant Examiner—Cecilia Shen
Attorney, Agent, or Firm—Mark A. Montgomery

[57] ABSTRACT

Interchange reactions between organosulfides and mercaptans are promoted by the use of catalysts containing tungsten and molybdenum oxide.

17 Claims, No Drawings

SULFIDE METATHESIS

BACKGROUND

Organosulfides are useful in a number of ways. Many sulfides are solvents, plasticizers and processing aids for various other organic materials. Some diorganosulfides, such as phenylpropylsulfide, are useful as corrosion inhibitors, hair growth stimulators, and as extractants for noble metals.

The preparation of organosulfides using mercaptans as reactants involves a metathesis, or interchange, reaction between the organic radical of the mercaptan and one or more of the organic substituents of an organosulfide reactant. Such reactions generally have low conversion and selectivity values.

INVENTION

It has been discovered that the reaction of certain organosulfides with mercaptans to yield substitution, or metathesis, products, can be more effectively carried out in the presence of Group VIB oxides, specifically supported phosphotungstic or phosphomolybdic acid catalyst.

In one embodiment, alkyl aryl sulfides are prepared from thiophenol by reacting it with dialkyl sulfides over an alumino phosphotungstic acid catalyst. For example, when a mixture of a di-n-propyl sulfide and thiophenol is passed over a hot (580° F.) catalyst prepared from aluminum phosphate and phosphotungstic acid, a 12% sulfide conversion results in a product having a 90.5% selectivity to phenyl n-propylsulfide.

OBJECTS OF THE INVENTION

It is one object of the invention to provide catalysts useful for assisting in the reaction of organic sulfides with mercaptans to yield metathesis or interchange products.

It is another object to provide a process by which such interchange reactions can be carried out.

Advantages

The catalysts and processes of the invention have several advantages over the prior art. Specifically, reactions carried out in accordance with the invention have good conversion rates and high selectivities to desired products.

Other advantages and aspects of the invention will become apparent from a consideration of the following description.

DESCRIPTION OF THE INVENTION

Reactants

The reactants with which the invention are concerned take part in interchange reactions involving mercaptans, i.e., thiols or thioalcohols, and sulfides, i.e., thioethers. Generally, these reactions involve interactions in which at least one organic moiety of a diorganosulfide is replaced by an organic moiety from a mercaptan.

The general reaction scheme is

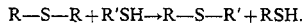

$$R-S-R + R'SH \rightarrow R-S-R' + RSH.$$

In the above formulas, R and R' are independently selected from the group consisting of alkyl, cycloalkyl, aromatic, alklaryl, arylalkyl, straight chain or branched chain groups, with the R's being the same or different in the same molecule. Generally, the R and R' groups are selected so that sulfides and mercaptans to be used contain from about 2 to about 40 carbon atoms per molecule, preferably from about 2 to about 16.

Sulfides useful in the invention are exemplified by the sulfides disclosed in U.S. Pat. No. 4,059,636, the disclosure of which is hereby incorporated by reference.

The organic sulfides employed in the practice of this invention include those of general formula R—S—R; wherein the R groups are as defined above.

Examples of useful sulfides include dimethyl sulfide, diethyl sulfide, diisopropyl sulfide, di-n-butyl sulfide, di-n-octyl sulfide, di-n-dodecyl sulfide, di-n-eicosyl sulfide, methyl ethyl sulfide, n-pentyl-n-heptyl sulfide, dicyclohexyl sulfide, bis(4-methylcyclohexyl)sulfide, diphenyl sulfide, di-p-tolyl sulfide, bis(p-n-hexylphenyl)sulfide, dibenzyl sulfide, and the like. Mixtures of sulfides as well as mixtures of sulfide with other inert components are feedstocks within the scope of this invention.

Useful mercaptans correspond to the sulfides discussed above. That is, they are of the formula R'SH in which R' is independently selected from the groups of moieties defined above.

Examples of useful mercaptans include alkylthiols, e.g., methyl mercaptan (methanethiol), ethyl mercaptan (ethanethiol), octyl mercaptan (octanethiol) and the like; aromatic thiol, e.g., phenyl mercaptan (thiophenol), napthyl mercaptans (napthylene thiols), and the like. Phenyl mercaptan and alkylphenyl mercaptans are preferred. Substituted forms of these mercaptans, i.e., compounds containing branched chain and/or nonfunctional substituents are operable. Mixtures of mercaptan reactants are operable.

While the use of stoichiometric quantities of reactants can be inferred from the above equation, quantities other than stoichiometric amounts are operable. Generally sulfide:mercaptan mole ratios of about 1:1 to about 1:10 with about 1:1.01 to about 1:5 preferred, can be used. While the presence of an excess of either reactant can be tolerated, it is preferred that, when excess reactant is used, it be the mercaptan (thiol) which is present in excess. This is primarily because of the relative ease of separation due to high volatility of the mercaptan and in part because of economics.

The use of more than one sulfide and mercaptan combination is contemplated.

Catalysts

The catalysts useful herein are derivatives of molybdic and tungstic components and are produced by contacting them with suitable supports.

Suitable tungsten oxide and molybdenum oxide components include phosphotungstic and phosphomolybdic acid, their hydrates, metal salts, and the like. Mixtures of molybdenum and tungsten oxide components can be employed.

One preferred catalyst is an aluminophosphotungstic acid prepared by reacting an aluminum-containing compound with phosphotungstic acid.

The catalysts can be used with or without a support. When supported, useful support components include activated carbon, alumina, aluminum phosphate, zinc aluminate, silica alumina, zirconia, silica, thoria, pumice but the preferred support is alumina, zinc aluminate or aluminium phosphate.

The amount of catalyst employed in the instant reactions generally ranges from about 0.01 weight percent to about 1 weight percent based on the weight of the total reaction mixture. The catalyst can be regenerated when necessary by heating and passing $H_2S$ over it at elevated temperature.

REACTION CONDITIONS

The metathesis reactions carried out in accordance herewith involve well-known reaction parameters. The following are merely suggestions from which the skilled artisan can extrapolate.

Useful reaction conditions for the inventive process include those under which conversions of the instant type occur, i.e., those under which, for example, dialkyl sulfides react with aromatic mercaptans to produce alkyl aryl sulfides.

If desired, an inert diluent can be employed in the feedstream to dilute or fluidize the feedstream. Such diluents may be especially desirable with higher molecular weight organic sulfides to facilitate flow to and from the reactor. Such diluents include hydrocarbons such as pentane, hexane, benzene, toluene, xylenes, etc. They can be used in any suitable amounts.

The above-described ingredients of the feedstream are intimately mixed by any suitable means and are then contacted with the catalyst in any suitable reaction zone under sulfide-cleaving conditions to produce the desired results. This invention is especially well suited for the use of a continuous reactor, but, if desired, a batch reactor can be employed.

Reaction temperatures can vary widely depending on other reaction conditions. Temperature can also depend on the reactivity of the sulfide feedstock and on the degree of sulfide cleavage desired. Generally, temperatures in the range of about 350° to about 700° F. (177° to 371° C.) are employed using presently available commercial catalysts. The use of the phosphotungstic acid catalyst permits good conversion and selectivity in a temperature range of about 350° to about 600° F. (177° to 315° C.). It is preferable, because of the principal reaction rate, side-reactions, etc., to employ temperatures in the range of about 450° to about 550° F. (232° to about 288° C.).

Reaction pressures can vary widely. Usually, pressures in the range of about 100 to about 5000 psig can be used, although, as a matter of convenience, pressures of about 150 to about 750 psig are normally preferred.

Contact time of the reactants with catalyst under suitable sulfide-cleaving condition can vary widely depending on desired degree of sulfide-cleavage and other reaction conditions. However, weight hourly space veocities (weight feed/weight catalyst/hour) in the range of about 0.1 to about 10, and preferably about 0.4 to about 2, are normally employed.

The following examples illustrate the invention.

EXAMPLE I

This example describes the preparation of the catalysts employed in this invention. A mixture of 100 grams of zinc aluminate, 1.27 grams phosphomolybdic acid and 200 milliliters of water was stirred at ambient room temperature for two hours after which the water was removed under vacuum at 90°–100° C. The wet catalyst was further dried and activated according to the procedure described in Example II.

Another catalyst system was similarly prepared from 27 grams of aluminum phosphate (containing 1 percent chromic and boric acid), 5 grams of phosphotungstic acid and 15 milliliters of methyl alcohol.

EXAMPLE II

This example describes two inventive runs employing the catalysts as prepared in Example I. A stainless steel tubular reactor with heaters (0.5 inch diameter × 18 inch length) was charged with 10 milliliters of glass beads, 50 grams (70 milliliters) of wet catalyst from Example I, and another 10 milliliters of glass beads. The system was purged with nitrogen at 316° C. (600° F.) to dry the catalyst and activated by passing $H_2S$ over the catalyst for 4 hours at 316° C./100 psig/ The reactor contents were then maintained at about 304° C. (580° F.)/450 psig while a mixture of thiophenol and di-n-propyl sulfide at a mole ratio of about 1.04:1 was metered through the reactor at 2 milliliters/minute using a LS-30 Lapp pump. On the downstream side, pressure was controlled and products removed by a Whitey 2 RF 2 valve operated by a Taylor Fulscope. A valved needle assembly was placed in the line after pressure let-down to provide intermittent sampling of liquid into cooled, capped Diels-Alder tubes. Samples were analyzed by GLC using a 12 foot × 0.125 inch column packed with 10% SE 30 on acid-washed dimethylchlorosilane treated chromosorb programmed at 30 degrees per minute between 50° C. and 300° C. The results are listed in Table I for the two catalysts studied. These results show both catalyst systems effective in producing n-propyl phenyl sulfide from di-n-propyl sulfide and thiophenol, the phosphomolybdic acid catalyst giving a higher di-n-propyl sulfide conversion and a higher n-propyl phenyl sulfide selectivity than the phosphotungstic acid catalyst.

TABLE I

Preparation of n-Propyl Phenyl Sulfide From
Di-n-Propyl Sulfide and Thiophenol
Temp. 304° C. (580° F.)
Press. 450 psig

| Catalyst | Thiophenol | | Di-n-Propyl Sulfide | | Percent | |
|---|---|---|---|---|---|---|
| | Grams | Moles | Grams | Moles | Conv. | Selectivity |
| 1. Phosphotungstic Acid on Aluminum Phosphate | 330 | 2.995 | 340 | 2.875 | 12.3 | 90.5 |
| 2. Phosphomolybdic Acid on Zinc Aluminate | 330 | 2.995 | 342 | 2.892 | 51.4 | 94.1 |

Reasonable variations, such as those which would occur to the skilled artisan, may be made herein without departing from the scope of the invention.

I claim:

1. A process for the reaction of organosulfides with mercaptans which comprises:

contacting a feed consisting essentially of organosulfide and mercaptan in the presence of a catalyst which contains a reaction product of a Group III A component and a phospho Group VIB reactant under reaction conditions to exchange one organic moiety of the organosulfide with the hydrogen of the mercaptan.

2. The process of claim 1 wherein the phospho Group VIB reactant is phosphotungstic acid.

3. The process of claim 2 wherein the Group IIIA component is an aluminum-containing substance.

4. The process of claim 3 wherein the aluminum-containing substance is aluminum phosphate.

5. The process of claim 4 wherein the organosulfide is a dialkyl sulfide and the mercaptan is an aromatic mercaptan.

6. The process of claim 1 wherein the mercaptan is thiophenol and the dialkyl sulfide is di-n-propyl sulfide.

7. The process of claim 1 wherein the phospho Group VIB reactant is phosphomolybdic acid.

8. The process of claim 7 wherein the Group IIIA component is an aluminum-containing substance.

9. The process of claim 8 wherein the aluminum-containing substance is zinc aluminate.

10. The process of claim 9 wherein the organosulfide is dialkylsulfide.

11. The process of claim 10 wherein the mercaptan is an aromatic mercaptan.

12. The process of claim 11 wherein the mercaptan is thiophenol and the dialkylsulfide is di-n-propylsulfide.

13. The process of claim 1 wherein the process is carried out under pressure in the range of about 100 to about 5,000 psig and in the temperature range of about 350° F. to about 700° F.

14. The process of claim 13 wherein the process is carried out in a diluent at about 450 psig and at about 600° F.

15. A process for the reaction of organosulfides with mercaptans which comprises:
    contacting an organosulfide with a mercaptan in the presence of a catalyst which contains a reaction product of a Group IIIA component and a phospho molybdic reactant under reaction conditions to exchange one organic moiety of the organosulfide with the hydrogen of the mercaptan.

16. A process for the reaction of organosulfides with mercaptans which comprises:
    contacting an organosulfide with a mercaptan in the presence of a phospho Group VIB reactant on a support selected from the group consisting of metal aluminate and Group IIIA phosphate, under reaction conditions to exchange one organic moiety of the organosulfide with the hydrogen of the mercaptan.

17. A process for the reaction of organosulfides with mercaptans which comprises:
    contacting di-n-propylsulfide with thiophenol in the presence of a catalyst which contains a reaction product of a Group IIIA component and a phospho Group VIB reactant under reaction conditions to exchange one organic moiety of the organosulfide with the hydrogen of the mercaptan.

* * * * *